United States Patent [19]

Fass et al.

[11] Patent Number: 5,278,069

[45] Date of Patent: Jan. 11, 1994

[54] BIOLEACHING METHOD FOR THE EXTRACTION OF METALS FROM COAL FLY ASH USING THIOBACILLUS

[75] Inventors: Raphael Fass, Ramat-Aviv; Joseph Geva, Ramat Hasharon; Zamir P. Shalita, Ramat-Gan; Moshe D. White, Rishon Lezion; Joseph C. Fleming, Nes Ziona, all of Israel

[73] Assignee: The Israel Electric Corporation Ltd., Haifa, Israel

[21] Appl. No.: 855,322

[22] Filed: Mar. 20, 1992

[30] Foreign Application Priority Data

Feb. 14, 1992 [IL] Israel ................................. 100950

[51] Int. Cl.$^5$ ........................... C12S 1/00; C12P 3/00; C12N 1/00
[52] U.S. Cl. .................... 435/262; 435/821; 435/168
[58] Field of Search ............ 435/262, 821, 168; 423/DIG.

[56] References Cited

U.S. PATENT DOCUMENTS 3,982,955 9/1976 Yen et al. ............................ 435/281
4,729,788 3/1988 Hutchins et al. ............ 423/DIG. 17

OTHER PUBLICATIONS

Ebner, H. "Metal Recovery and Environmental Protection . . . " Cas Abstract CA89(22):182969r.
Wilczok et al. "Bioextraction of Copper and Zinc from Coal Fly Ash" CAS Abstract CA106(13):99099f.
Bosechen, K. "Microbial Recycling of Mineral Waste Products" Biosis Abstract 88:160271.
Furuya, K. et al. (1987), Environ. Sci. Technol. 21, pp. 898-903.
Golden, D. M. (1986), Energy 11 (11/12) pp. 1377-1387.
Baldensperger J. et al. (1974), Arch. Microbiol. 99, pp. 323-329.
Boker (1987), I.E.C. Report ECD-87-6.
Shendrikar and Ensor (1986), Adv. Environ. Sci. Technol. 17, pp. 53-111.

*Primary Examiner*—Michael G. Wityshyn
*Assistant Examiner*—T. J. Reardon
*Attorney, Agent, or Firm*—Helfgott & Karas

[57] ABSTRACT

A bioleaching process is utilized for the extraction of metals from coal fly ash (CFA). The CFA is suspended in an acidic sea water based culture medium and the suspension is incubated with a microorganism culture comprising at least one strain of *Thiobacillus thiooxidans* capable of growing and producing sulfuric acid in the sea water based acidic culture medium and thereby facilitating the extraction of metals from the CFA. The extracted metals are separated from the CFA raffinate and microorganism cells and are fractionated to provide metal-enriched fractions. A selected *Thiobacillus thiooxidans* strain is described which has been designated as *Thiobacillus thiooxidans* ZYR1, a sample of which has been deposited under No. 40453 at the National Collections of Industrial and Marine Bacteria Ltd. (NCIMB) at Aberdeen, Scotland. This selected strain is particularly suitable for the bioleaching of metals from coal fly ash.

16 Claims, 4 Drawing Sheets

BIOLEACHING METHOD FOR THE EXTRACTION OF METALS FROM COAL FLY ASH USING THIOBACILLUS

FIELD OF THE INVENTION

The present invention is generally in the field of biotechnological methods for the extraction of metals from industrial wastes containing such metals.

More specifically, the present invention concerns a bioleaching method for the extraction of valuable metals such as, for example, aluminium and titanium, from coal fly ash (hereinafter "CFA"), which is the waste product of coal-fired power stations. By the process of the present invention the metals contained in the CFA are solubilized, recovered and subsequently purified to provide valuable metal compounds, e.g. salts, and also as a by-product, detoxified CFA, i.e. CFA from which toxic metals have been extracted, which can then be safely disposed of in landfills or used as, for example, a soil fertiliser.

The present invention also concerns Thiobacillus strains, in particular *Thiobacillus thiooxidans* strains which are useful for carrying out the above bioleaching method of the present invention.

BACKGROUND OF THE INVENTION AND PRIOR ART

CFA is known to contain a variety of metals such as aluminium (Al), titanium (Ti), zinc (Zn), copper (Cu), cobalt (Co), molybdenum (Mo), selenium (Se), boron (B) and many others, usually in the form of insoluble metal-silicates or -oxides (Furuya, K. et al (1987), Environ. Sci. Technol. 21, p.898–903). Many of these metals are toxic to living organisms. Thus, when CFA is disposed of in landfills, in the sea or in other waterways, these metals may leach out of the CFA and enter sources of water for plants and animals including humans. Thus, the various metals contained in CFA represent a potential environmental and health hazard.

Globally, millions of tons of CFA are disposed of annually in industrialised countries, representing a serious potential for environmental pollution and subsequent public health hazard. Power-producing utilities using coal as the energy source are therefore required to safely dispose of the CFA produced as a by-product.

However, the conventional means for detoxifying CFA for the purposes of safely disposing it are both costly and may in themselves also lead to environmental pollution, for example the use of conventional chemical leaching, usually by way of strong acids and at high temperatures (Golden, D. M. (1986) Energy, vol. 11, No. 11/12, p. 1377–1387), requires both costly machinery and chemicals on the one hand, and on the other, chemical by-products, for example strong acids, are produced which must also be disposed of and as such also represent a potential environmental and health hazard.

It has therefore been a long-felt want to establish a process for the detoxification of CFA, by removing therefrom the toxic metals, which is both economically feasible, i.e. allows for the extraction of valuable metals, e.g. aluminium, titanium, cobalt, etc. in commercial quantities, and which does not itself lead to the generation of toxic by-products.

While it has been previously contemplated to use various acid producing bacteria, e.g. Thiobacillus strains in bioleaching methods to extract metals from various metal-bearing sources, none of these methods have been directed specifically to the bioleaching of CFA, nor have any of these methods been successful in generating safely disposable by-products, i.e. they all result in the generation of strong acids which require further expensive and time consuming neutralization treatments.

As noted above, CFA contains a number of toxic metals and thus microorganisms suitable for the bioleaching of CFA must be capable of growing in the presence of these toxic metals.

Furthermore, many coal-fired power stations worldwide are situated at coastal locations with the result that the CFA to be detoxified is often present in sea water, e.g. in consequence of dumping into sea water precipitation pools. Accordingly, microorganisms suitable for bioleaching this CFA must also be capable of growing in a sea water environment, i.e. in the presence of a relatively high salt concentration.

• It has heretofore not been disclosed that an acid-producing microorganism suitable for the bioleaching of CFA, e.g. a Thiobacillus strain may be obtained that is capable of growing in a sea water based medium in the presence of CFA.

OBJECT OF THE INVENTION

It is an object of the present invention to provide an environmentally friendly and commercially viable process for the bio-extraction of metals from CFA. Such a bio-extraction or bioleaching process is to be carried out by selected microorganism strains which are capable of growing in the presence of the toxic metals present in CFA and extracting these metals from the CFA to provide detoxified CFA which can then be safely disposed.

It is a further object of the present invention to provide for the recovery of commercially valuable metals from CFA, for example aluminium and titanium.

It is yet another object of the present invention to provide a microorganism strain or a mixture of microorganism strains that are useful for carrying out the above bioleaching process.

SUMMARY OF THE INVENTION

The present invention is based on the surprising finding that some strains of the sulfuric acid producing *Thiobacillus thiooxidans* are capable of growing in a saline culture medium having a nitrogen source for the bacteria, in which there is suspended 10–50% w/v of coal fly ash (CFA) mixed with about 1% precipitated sulfur, and that in this growth medium the *Thiobacillus thiooxidans* strains are capable of producing sulfuric acid which in turn leads to the solubilization of metals contained in CFA, such as aluminium, titanium, vanadium, selenium, boron, molybdenum, cobalt and others.

The present invention therefore provides a bioleaching process for the extraction of metals from coal fly ash (CFA) comprising the steps:

(a) producing an acidic culture medium by incorporating in a sea water solution a nutrient supplement including at least a nitrogen source, suspending therein CFA in the amount of 10–50% w/v and adding sulfuric acid until an initial pH within the range of about 2.5 to about 4.0 is attained;

(b) innoculating into said culture medium a microorganism culture which comprises at least one strain of *Thiobacillus thiooxidans* capable of growing and producing sulfuric acid in said acidic culture medium;

(c) establishing aerobic conditions in the innoculated culture medium by aeration and agitation and maintaining aerobic conditions to induce fermentation until the pH of the fermentation culture decreases to a level at which the leachable metals are leached from said CFA;

(d) interrupting the aeration and agitation to enable separation of said fermentation culture into a CFA raffinate sediment and a supernatant comprising a suspension of the *Thiobacillus thiooxidans* cells and the extracted metals, and separating the supernatant from the sediment;

(e) subjecting the said supernatant to microfiltration to separate the Thiobacillus thiooxidans cells whereby a metal-bearing filtrate and a concentrated suspension of the *Thiobacillus thiooxidans* cells are separately obtained;

(f) fractionating the metal-bearing filtrate by stepwise raising the pH thereof by the addition of a desired amount of a suitable base to precipitate a metal containing fraction, and collecting a metal containing fraction after each precipitation.

In accordance with one embodiment of practising the present invention, said at least one *Thiobacillus thiooxidans* strain is derived from a natural environment. In that case, the nutrient supplement should preferably contain, in addition to the nitrogen source, also phosphate and sulfur sources and, if desired, also a surfactant, a typical nutrient supplement composition for such an embodiment being potassium phosphate, ammonium sulfate, elemental sulfur and the surfactant Tween-80 TM.

In accordance with another embodiment of practising the present invention, there is used a selected, CFA acclimatized *Thiobacillus thiooxidans* culture previously grown for an extended period in a sea water culture medium in the presence of CFA. Such a selected culture does, as a rule, not require potassium and phosphate supplements, these being available to the acclimatized culture from the CFA and the sea water, nor the addition of a surfactant and in that embodiment a nitrogen source supplement, e.g. ammonium nitrate is, as a rule, sufficient. An example of such an acclimatized culture is the concentrated *Thiobacillus thiooxidans* cell suspension obtained from step (e) above. This concentrated cell suspension may be recycled and used as the microorganism culture in step (b) above in a second and any subsequent process cycle.

In both the above embodiments, the amount of CFA incorporated in the culture medium is about 10–50% w/v and preferably 10–20% w/v.

The microorganism culture innoculated into the culture medium in accordance with step (b) above, if not recycled as specified, is made from a starter culture which is prepared by growing a suitably selected *Thiobacillus thiooxidans* culture in an acidic sea water solution with nutrient supplement in the absence of CFA. When this culture has reached a desired cell count, e.g. of about $2 \times 10^9$ cells/ml, and a low pH indicative of optimal cell growth and sulfuric acid production of about 1.2–1.5, it is subjected to microfiltration using a commercial microfilter of 0.45 $\mu$m or preferably 0.22 $\mu$m to provide a concentrated cell suspension which is the culture used for innoculation in the above step (b). The filtrate from this microfiltration is acidic.

Preferably, the CFA introduced into the culture medium is first washed with acidic aqueous solution and when a starter culture is made as specified above, the filtrate resulting from the microfiltration of the starter culture is used for the purpose. The preliminary washing of the CFA serves, among others, to remove hydroxide ions usually present in CFA and which, if they were to remain, would raise the initial pH of the fermentation culture leading to a slow initial growth of the cells or alternatively necessitate the addition of a relatively large amount of sulfuric acid to lower the pH of the culture medium to the desired initial value of 2.5–4.0.

If desired, the filtrate of the starter culture may be used for washing in admixture with native sea water. For example, a mixture of 20% v/v acidic starter culture filtrate and 80% v/v sea water is used for washing the CFA. In this way the pH of this filtrate is raised to neutral or near-neutral which enables its disposal in an environmentally friendly manner which is a further benefit.

As indicated above, in second and subsequent rounds of the bioleaching process, the said starter culture may be augmented or even replaced by the concentrated cell suspension obtained in step (e) of the first round of the process.

The fermentation step of the above process may be terminated when the fermentation culture of the above noted step (c) has reached a value below 2.0, e.g. about 1.5 or less. It is preferable to allow the above fermentation step to continue until the pH of the fermentation culture has reached a value of between 0.4 and 1.0, more preferably a value of between 0.6 and 0.8.

The separation of the supernatant and CFA raffinate sediment of step (d) of the above process may be carried out by either decantation of the supernatant, or by filtration with a filter of a mesh size sufficiently large to allow passage of the cells and the extracted metals, and sufficiently small to block passage of the CFA raffinate sediment.

Typically, the CFA raffinate sediment is washed twice, e.g. with sea water, and preferably with agitation, before being disposed of, in order to remove extracted metal entrapped in the sediment. The first wash water is recycled and combined with the metal-bearing filtrate of step (e) for subsequent precipitation of a metal bearing fraction therefrom (step (f)).

Step (e) is usually performed by microfiltration with a commercial microfilter of 0.45 $\mu$m or preferably 0.22 $\mu$m to obtain a metal-bearing filtrate and a concentrated cell suspension. The metals in this filtrate are typically dissolved and solubilized metal salts and if aggregated the aggregates are relatively small, i.e. can pass through the above 0.45 $\mu$m or preferably a 0.22 $\mu$m filter. Any extracted metals being trapped in the concentrated cell suspension may be removered either by washing the cell suspension under agitation with sea water and refiltering through the same microfilters, or by recycling the concentrated cell suspension by innoculating it into the said culture medium in accordance with step (b) above.

Step (f) of fractional precipitation is performed with a suitable base such as aqueous KOH or NaOH, e.g. a 10N aqueous NaOH solution. As noted above, this precipitation may be carried out on the metal-bearing filtrate of step (e) or, if desired, on the mixture of this metal-bearing filtrate and the first wash water of the washed CFA raffinate.

The present invention also provides a *Thiobacillus thiooxidans* culture useful for carrying out the above process. This culture comprises at least one strain of *Thiobacillus thiooxidans* which is capable of growing in the supplemented sea water solution in which is suspended up to 50% CFA w/v, and having a pH of as low as pH 0.4.

By one embodiment of this aspect of the invention there is provided a *Thiobacillus thiooxidans* culture derived from a mixed culture of three *Thiobacillus thiooxidans* strains, designated herein strains C, D and G, which mixed culture is capable of growing in the aforesaid culture conditions.

By another embodiment of this aspect of the invention, there is provided a *Thiobacillus thiooxidans* strain, designated herein as strain M, which has been derived from the aforesaid mixed culture of strains C, D and G. A sample of this strain has been deposited at the National Collection of Industrial and Marine Bacteria, Aberdeen, Scotland (NCIMB) under Accession No. 40453 and has been designated *Thiobacillus thiooxidans* ZYR 1.

The preferred modes of carrying out the above process of the invention are set forth hereinbelow, from which it is concluded that the process of the invention provides an economically feasible and environmentally friendly way in which CFA may be detoxified.

DETAILED DESCRIPTION OF THE INVENTION

Figure 1:
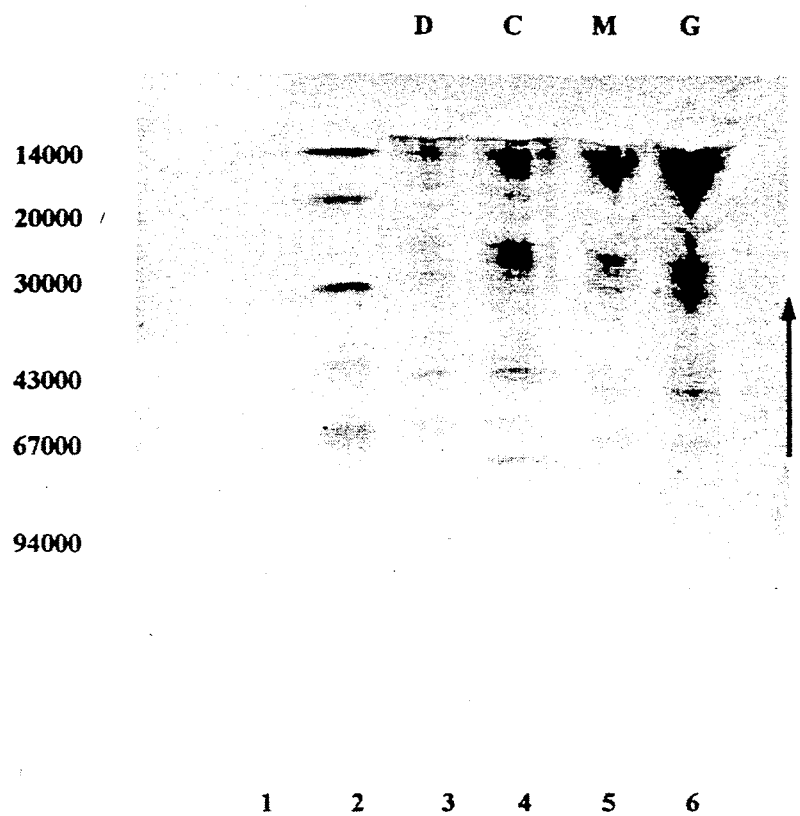
FIG. 1 is a representation of a gel electrophoresis analysis of the various *Thiobacillus thiooxidans* strains according to Example 5.

The invention will now be described in more detail in the following non-limiting examples and their accompanying Tables and Figures.

EXAMPLE 1

Sea water-based microorganism culture growth medium

Mediterranean sea water was repeatedly pumped from about 30 m from the same sea shore site, namely, Palmahim beach near Nes Ziona, Israel. The sea water composition was frequently monitored, and its typical elemental composition is presented in Table 1. The sea water was supplemented with 3.5 g/L—$KH_2PO_4$, 0.2–0.3 g/L—$NH_4SO_4$, 10 g/L elemental (i.e. precipitated powder) sulfur and 0.2 ml/L—Tween-80 TM to provide the basic sea water-based growth medium, SSW, the typical elemental composition thereof also being presented in Table 1. It should be noted that the aforesaid sea water-based medium corresponds to that disclosed in Baldensperger, J. et al., Arch. Microbiol. 99, 323–329 (1974).

Each 100 ml of the above sea water-based medium was prepared by solubilizing all of the components in 900 ml sea water except the sulfur and then filtering the solution with a 0.22 μm filter. The sulfur is prepared separately as a suspension in 100 ml sea water and added to the above filtered solution. The sulfur used generally did not have any contaminants, but for the sake of preventing any contamination the sulfur suspension is boiled in steam for about 30 min. This steaming may be repeated for three consecutive days. The steamed sulfur suspension was then added to the above filtered solution to give the final sea water-based medium, usually having a pH adjusted to be about pH 3.0, the chemical composition of which is set forth in Table 2. A tap water-based growth medium is also presented in Table 2 as a comparison to the sea water-based medium, this tap water-based medium having been used as the original medium for growing some of the microorganism strains. Thus, as is apparent from Table 2, magnesium sulphate, calcium chloride and iron sulphate present in the tap water-based medium may be omitted from the sea water-based medium. Further, the potassium phosphate may also be omitted from sea water-based medium containing coal fly ash (CFA).

The above sea water-based medium was used for the selection procedure to obtain the desired microorganisms. However, once selected strains were obtained no special treatment of sulfur and no aseptic procedures, as noted above, were required for preparing the media for routine growth of the selected strains. The media prepared for bioleaching process as set forth in the following Examples, also did not require sulfur treatment or aseptic procedures, rather a mixing together of all the media components as indicated above.

In some experiments to analyse the ability of the microorganisms to grow in sea water in the presence of coal fly ash (CFA), the sea water-based medium was prepared by supplementing the aforesaid sea water with only 1.0 g/L ammonium nitrate, as nitrogen source.

TABLE 1

| Chemical composition of sea water (Palmahim) and their derived sea water based medium (SSW) | | |
|---|---|---|
|  | Sea Water g/L | SSW g/L |
| Sodium | 14.0 | 14.0 |
| Potassium | 0.50 | 1.60 |
| Boron | 0 | 0 |
| Calcium | 0.514 | 0.549 |
| Aluminum | 0 | 0 |
| Magnesium | 1.6 | 1.6 |
| Iron | 0 | 0 |
| Titanium | 0 | 0 |
| Zinc | 0.014 | 0.014 |
| Nickel | 0 | 0 |
| Molybdenum | 0 | 0 |
| Copper | 0.0075 | 0.0043 |
| Cobalt | 0 | 0 |
| Cadmium | 0 | 0 |
| Chrome | 0 | 0 |
| Sulfate | 3.39 | 3.39 |
| Phosphate | 0.013 | 2.4 |
| Selenium | 0 | 0 |
| Arsenic | 0 | 0 |
| Mercury | 0 | 0 |
| Vanadium | 0 | 0 |
| Manganese | 0 | 0 |

TABLE 2

| Composition of media for Thiobacilli growth | | |
|---|---|---|
| Component | TAP Water Based (g/L) | SEA Water Based (g/L) |
| $(NH_4)_2 SO_4$ | 0.2 | 0.2 |
| $Mg\ SO_4.7H_2O$ | 0.5 | — |
| $CaCl_2$ | 0.25 | — |
| $KH_2 PO_4$ | 3.5 | 3.5 |
| $Fe\ SO_4$ | 0.005 | — |

TABLE 2-continued

| Composition of media for Thiobacilli growth | | |
|---|---|---|
| Component | TAP Water Based (g/L) | SEA Water Based (g/L) |
| Tween-80 TM | 200 μL | 200 μL |
| Sulfur (precipitated) | 10.0 | 10.0 |

EXAMPLE 2

Coal Fly Ash (CFA)

The CFA was derived from coal burnt at the "Maor David" power plant, Hadera, Israel. Samples were taken from piles of CFA which were well mixed. The typical metal oxide composition of these CFA samples is presented in Table 3 (see Boker, Y. IEC Report ECD-87-6, of Israel Electric company, 1987). Besides these metal oxides, the CFA also contains various metals such as Cd, Cu, Ni, Co, Cr, Zn, Va, Mo, Se, B and others which are toxic for various microorganisms, plants and animals.

TABLE 3

| Chemical composition of oxides in coal fly ash (CFA) | |
|---|---|
| Oxide | % |
| $SiO_2$ | 48 |
| $Al_2O_3$ | 30 |
| $Fe_2O_3$ | 5.7 |
| CaO | 7.2 |
| MgO | 2.5 |
| $TiO_2$ | 1.3 |
| $K_2O$ | 0.6 |
| $Na_2O$ | 0.4 |
| $SO_3$ | 3.7 |
| $P_2O_5$ | 0.9 |

EXAMPLE 3

Source of Microorganism strains

Three original strains of *Thiobacillus thiooxidans* were obtained from the following sources:
1) Strain C: *Thiobacillus thiooxidans* Vulc 6T, isolated from thermal water (Sulfatara, near Naples, Italy). This strain was obtained from the Federal Institute for Geosciences and Natural Resources, Hannover, Germany.
2) Strain D: *Thiobacillus thiooxidans* Ram 8T, isolated from mining water in the Harz Mountains, near Hannover, Germany. This strain was also obtained from the Federal Institute for Geosciences and Natural Resources, Hannover, Germany.
3) Strain G: *Thiobacillus thiooxidans* strain which was deposited at the American Type Culture Collection (ATCC), Rockville, Md., USA, under Accession No. ATCC 8085. This strain was purchased from the ATCC.

EXAMPLE 4

Isolation and Selection of a *Thiobacillus thiooxidans* strain capable of growing in a sea water-based medium containing CFA and suitable for the bioleaching of metals from CFA A culture medium composed of a suspension of 50% w/v CFA (Example 2) in sea water medium (Example 1) was inoculated with a mixture of the three original strains (Example 3). This mixed culture was grown for more than 4 months for the purpose of selecting a viable *Thiobacillus thiooxidans* strain capable of growing under the above conditions, namely in a saline environment and in the presence of various toxic metals or metal oxides present in the CFA, namely $Al_2O_3$, $TiO_2$, Mo, Se, B, Ni, Cu, Co and Cr, etc. as noted in Example 2. Viability of at least some of the bacteria in the mixed culture was observed by way of a decrease in the pH after 2 months incubation, from the initial pH of about 3.0 to reach a pH of 0.4 after 3 months incubation. This pH decrease is indicative of sulfuric acid production by the remaining viable bacteria in the culture. The culture was maintained for at least a further 1 month in the same medium, i.e. the surviving viable bacteria remain under the selective pressure brought about by the presence of the above-noted toxic metals in the medium, in particular the aluminium present in an amount of at least 4,000 ppm. The surviving viable bacteria were then transferred to fresh medium containing CFA and incubated for further periods of at least 7 days to allow for growth of the selected viable bacteria.

These further incubation periods or growth cycles typically were carried out in the above-noted sea water medium in the presence of 50% w/v CFA, the initial pH of the culture medium being about pH 3.0, and each inoculation of fresh medium being by way of 10% v/v of the previous culture that was grown for between 7-14 days (or in the case of the original culture, for about 4 months). At the end of the above growth cycles (at least 3 such cycles are necessary following the original culture of the mixed strains), a final mixed culture was obtained, characterized by containing selected *Thiobacillus thiooxidans* bacteria which are capable of growing in (i) a sea water based growth medium, (ii) in the presence of toxic metals and metal oxides in amounts as present in the CFA added to the growth medium (50% w/v); and (iii) in the acidic conditions of culture, namely, initially pH 3.0 which decreases to about pH 0.4 to about 0.8 after long incubation periods (one month or more), these pH decreases as a result of sulfuric acid production by the viable growing bacteria.

A strain of the Thiobacilli of the above selected mixed culture was termed strain M to distinguish it from the aforementioned parental strains. A sample of a pure culture of this strain M was deposited at the National Collection of Industrial and Marine Bacteria (NCIMB) under Accession No. NCIMB 40453 on Nov. 4, 1991, and was designated as *Thiobacillus thiooxidans* ZYR 1.

A number of experiments were also carried out to determine the optimum growth conditions for the *Thiobacillus thiooxidans* strain M. These revealed that optimized growth of these Thiobacilli was achieved in the sea water based medium supplemented with 1% elemental sulfur, ammonium nitrate (1 g/L), and up to 50% CFA, at pH values of about 3.0 initially. Furthermore, it was noted that the Tween-80 TM added initially to the growth media in a concentration of 200 μl/L—(i.e. 200 ppm) enhanced the sulfur miscibility in water and thus increased the rate of bacterial growth. This effect was less pronounced in subsequent cultures containing CFA which were initiated by inoculation with 10% v/v of the initial cultures.

EXAMPLE 5

Comparative Analysis of *Thiobacillus thiooxidans* strain M (NCIMB 40453) versus the original *Thiobacillus thiooxidans* strains C, D and G (a) As set forth in Example 4, strain M was selected after repeated growth of a mixed culture initiated by inoculation of sea water medium containing 50% w/v CFA of the three original strains C, D and G. In test experiments strains C, D, G and M were separately grown in the aforementioned sea water medium containing 10% w/v CFA.

It was observed that while strain M grew well and strain G was capable of growing under these conditions, both strains C and D failed to grow in the presence of 10% CFA. It should, however, be noted that while strains C and D did not grow in the presence of 10% CFA, namely in the presence of the various metals and/or metal oxides present in this CFA, data provided by Dr. Bosecker of the Federal Institute for Geosciences and Natural Resources, Hannover, Germany, the source of these strains, indicates that non-induced/non-adapted strains C and D can grow in the presence of 1,000 ppm Cu, Ni and Cr, strain D being viable even in the presence of 50,000 ppm Ni. This therefore indicates that strain M is likely to be a new *Thiobacillus thiooxidans* strain, being a derivative of the original mixture of strains C, D and G, and characterized by being resistant to metals and/or metal oxides present in CFA additional to Cu, Ni and Cr, e.g. resistant also to Al, Ti, Co, Se, Mo, B, Va, etc. In this regard it should be noted that strain M is still viable in the presence of 10,000 ppm Al.

(b) In protein profile analysis experiments, the proteins produced by the *Thiobacillus thiooxidans* strains C, D, G and M were analysed by SDS polyacrylamide gel electrophoresis (SDS-PAGE).

Each of the strains was grown in 500 ml of sea water medium (without CFA) pH 2.5–3.0 in 2000 ml culture flasks, with agitation and at a temperature of 30° C. for 48 hours. 300 ml of these cultures were then concentrated (750×) by centrifugation and the concentrated cells resuspended in a 200 μl 0.9% NaCl solution (in $H_2O$). The resuspended cells were centrifuged (Eppendorf), the supernatant discarded and the pelleted cells resuspended in 100 μl SDS buffer containing 10 mM Tris, 1.0 mM EDTA, 2.5% SDS, pH 8.0. The resulting whole cell suspensions were boiled for 5 min. and β-mercaptoethanol added to a final concentration of 5%. Samples from each of the boiled whole cell suspensions were loaded at about 1 μl per sample well of a polyacrylamide gel in a rapid electrophoresis apparatus (Pharmacia, Sweden), and electrophoresis was carried out at 65 V for 1 hr. A molecular weight marker control sample was also included in the above electrophoresis run and contained the following proteins: α-lactalbumin-m.w. 14,400; trypsin-inhibitor-m.w. 20,100; carbonic anhydrase-m.w. 30,000; ovalbumin-m.w. 43,000; albumin-m.w. 67,000; and PHB-hydroxylase β-m.w. 94,000.

The electrophoresed protein bands were stained (Coomassie Brilliant Blue) and developed by standard techniques and the results are presented in FIG. 1. In FIG. 1 lanes 1 and 2 show the bands corresponding to the above molecular weight markers, the respective molecular weights being indicated on the left-hand side of the Figure, lanes 3–6 represent the bands corresponding to strains D, C, M and G, respectively, as indicated, and the arrow on the right-hand side of the Figure indicates the direction of migration of the proteins during the SDS-PAGE procedure. From FIG. 1 it is thus observed that the protein bands of the four strains are few in number, indicative of the relatively few proteins produced by each of the strains. Further, the protein band profile of strains C, D and G are only partially similar indicating that these strains are not closely related. However, it is noted that the protein band profile of strains G and M are very similar, indicating that strain M is probably derived from strain G.

It should be noted, however, that the above electrophoresis only allowed for protein separation over a distance of about 32 mm, and therefore any minor differences in the sizes of the proteins from strains G and M cannot be resolved in such an electrophoretic separation. Further, as the above strains analysed by SDS-PAGE were grown under non-selective conditions, i.e. in the absence of CFA and at relatively high pH (pH 2.5–3.0), i.e. cultures were not grown long enough to reach a low pH of between 0.4–0.8, the protein bands observed in FIG. 1 are indicative of proteins produced by strains under non-induced conditions and therefore any alteration in the proteins produced by the various strains, in particular strains G and M, under inductive conditions (CFA, low pH), could not be expected to be revealed in the above SDS-PAGE analysis.

Figure 2:
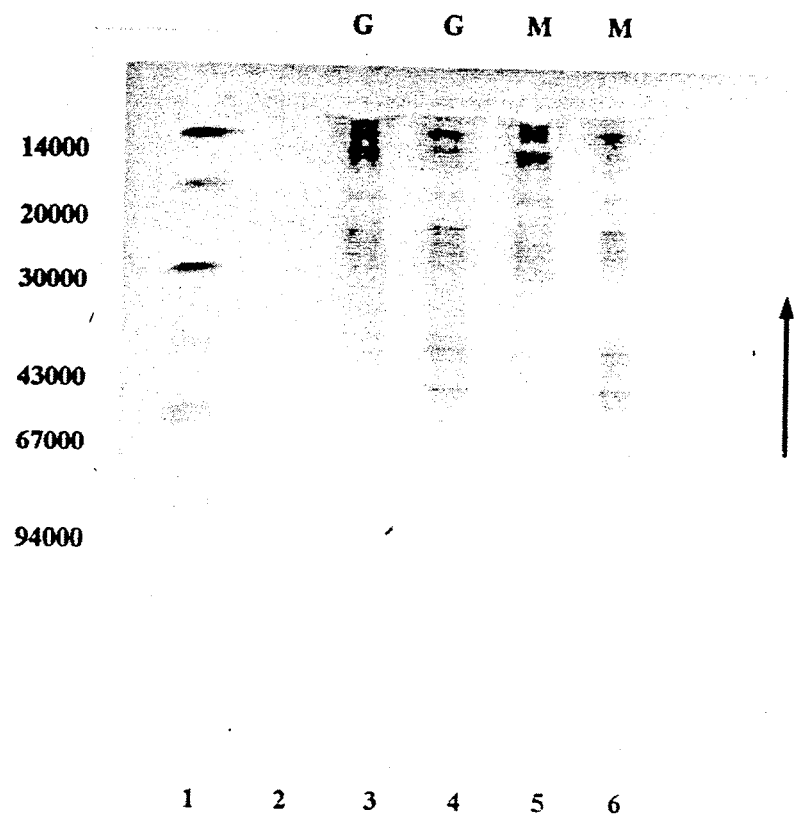
FIG. 2 is a representation of a gel electrophoresis comparative analysis between *Thiobacillus thiooxidans* strains G and M according to Example 5.

(c) Accordingly, a second SDS-PAGE analysis was carried out, the procedure of which was as noted above, but in which only strains G and M were compared and in which samples of induced strains G and M were included. Induction was performed by growing each of strains G and M separately in culture flasks with agitation (100 ml culture/500 ml culture flask), the culture medium (sea water medium) being supplemented with 50% w/v CFA and having pH 3.0. The cultures were incubated for at between 7–10 days at which stage the pH, as noted above, drops to between pH 0.6–0.8. Control cultures of strains G and M were grown in the same way but the culture medium did not contain CFA. The cultures were concentrated and samples were prepared for SDS-PAGE analysis as noted before. The SDS-PAGE gel in this analysis was a 10–15% gradient gel capable of providing good separation between protein bands of similar size. Further this gel also included high molecular weight protein markers: 67,000 m.w., 140,000 m.w., 232,000 m.w., 440,000 m.w. and 669,000 m.w., in addition to the above-noted lower molecular weight protein markers. In FIG. 2, lanes 1 and 2 show the bands corresponding to the above molecular weight markers, the respective molecular weights being indicated on the left-hand side of the Figure, lanes 3–6 represent the various samples from cultures of strains G and M where lanes 3 and 5 represent strains grown in the absence of CFA and lanes 4 and 6 represent strains grown in the presence of CFA, and the arrow on the right-hand side of the Figure indicates the direction of migration of the proteins during the SDS-PAGE procedure.

The results of this analysis as depicted in FIG. 2 indicate the following. No discernible differences were noted between strains G and M when both were grown in the presence of CFA (lanes 4 and 6—strains G and M, respectively). No discernible differences were noted between strains G and M when both were grown in the absence of CFA (lanes 3 and 5—strains G and M, respectively), this result in agreement with that depicted in FIG. 1, as noted above. However, differences are noted between the strains grown in the absence of CFA and in the presence of CFA (lane 3 vs. lane 4—strain G; and lane 5 vs. lane 6—strain M). These differences included a loss or reduction in the protein band at approximately 30,000 m.w. for strains grown in the presence of CFA along with an increase in intensity for a protein band at around 43,000 m.w. for strains grown in the presence of CFA. A similar increase in intensity, or possibly even new protein bands appear at just below 67,000 m.w. (the aforesaid m.w. determinations with respect to the marker proteins in lane 1—low molecular weight markers, as noted above; and lane 2—high molecular weight markers, as noted above).

Thus, in light of the above it may be concluded that both strains G and M produce larger amounts of or possibly even new proteins of approximate molecular weight 43,000, 67,000 and around 67,000 when grown in the presence of CFA as compared to when grown in the absence of CFA, and they stop producing or have a greatly reduced production of a protein or proteins of 30,000 m.w. when grown in the presence of CFA.

EXAMPLE 6

Maintenance of active stock cultures of the selected *Thiobacillus thiooxidans* strain M (NCIMB 40453) and routine culturing thereof The isolated selected strain M (Example 4) is maintained in stock cultures grown continuously in polypropylene shake flasks in the sea water-based growth medium (Example 2), supplemented with 10% w/v CFA, at 30° C. with agitation. Periodically, after incubation for periods of at least 7 days which leads to a decrease in the pH, due to normal sulfuric acid production by the bacterial cells, the pH of the cultures is adjusted back to pH 3.0 by the addition of ammonium hydroxide. Elemental sulfur is replenished to reach a final concentration in the culture of about 1% w/v at intervals of about 2 weeks. Usually these stock cultures are grown in 500 ml shake flasks, each containing 100 ml culture.

When cultures are to be used for the purposes of bioleaching CFA to extract therefrom the various metals, the above stock cultures of strain M are subjected to an induction or acclimatisation period by adding 10% v/v innoculum from the stock culture to fresh medium containing between 1-50% w/v CFA and adjusting the pH of the cultures to pH 2.5-3.0. When adding the CFA to prepare the above fresh media, the CFA is first flushed with between 0.05M to 0.1M sulfuric acid. In the case of flushing with 0.1M sulfuric acid, the flushed CFA when added to the culture medium brings about an adjustment of the pH to between about pH 3.0-4.0 and results in the promotion of cultures having a short log phase, i.e. the bacteria grow well and reach the log phase, or rapid growth phase, in a short period after inoculation.

These induced cultures are repeatedly analysed for their levels of growth and their bioleaching efficacy by standard determinations of bacterial counts and rate of pH decrease in the culture medium, i.e. sulfuric acid production in the culture; and the increase in the amount of dissolved, i.e. leached elements, by standard ICP assays according to the method disclosed in Shendrikar, A. D. and Ensor, D. S., Adv. Environ. Sci. Technol. 17, 53-111 (1986).

EXAMPLE 7

Fermentation systems

Two different fermentation systems are applied:
a) A 2.0 liter glass "Bioflo" Model C 30 fermentation system (New Brunswick Scientific, Edison, N.J., USA). This system was used for long term cultures, for introducing CFA into growing cultures (1-50% CFA w/v) and for preparing rapidly growing, log phase, cultures for inoculation of large scale fermentation cultures; and
b) A 14.0 liter "Magnaferm" fermentation system (New Brunswick Scientific, Edison, N.J., USA).

This system consists of a glass culture vessel topped with a polypropylene head plate, with a polypropylene agitation device and control probes mounted thereon.

Figure 4:
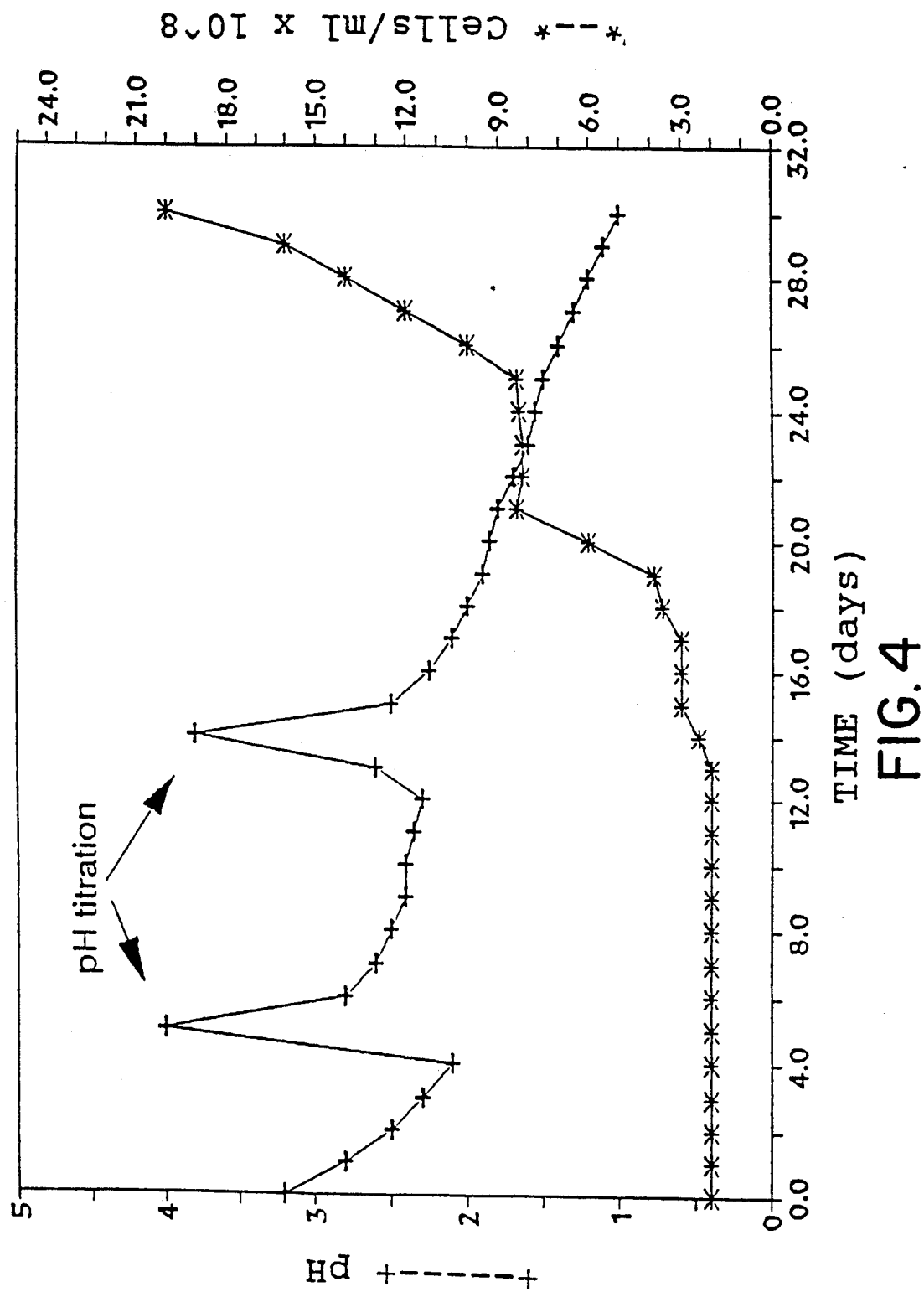
FIG. 4 is a representation of the fermentation process according to Example 7.

When growing cultures in either of the above fermentation systems, the temperature in the fermentors was maintained at 30° C., the pH was monitored and controlled, and the airflow and agitation speed were manually controlled to provide the desired levels supportive of maximal culture growth and cell viability. A typical fermentation profile is presented in FIG. 4 which shows that between days 14-30 of cell culture there is a marked increase in the number of cells in the culture together with a steady decline in the pH of the culture medium associated with growing viable cells which release sulfuric acid into the culture medium.

EXAMPLE 8

Bioleaching process

In the following a typical bioleaching process is described in which CFA is leached to extract metals therefrom by the action of the growing *Thiobacillus thiooxidans* strain M cells (NCIMB 40453) (Example 4). A flow diagram of this process is presented in FIG. 3.

Figure 3:
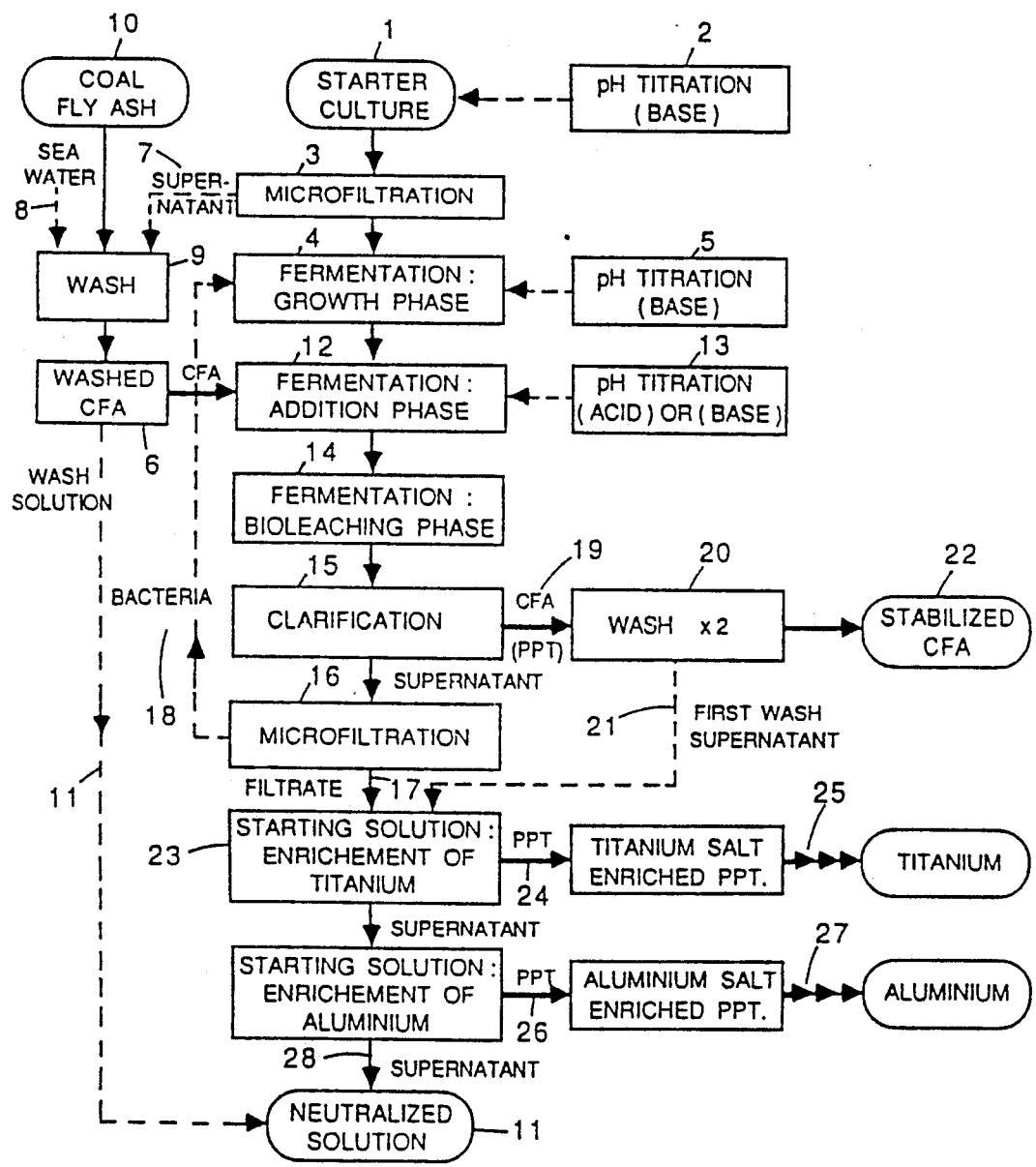
FIG. 3 is a flow diagram of the process of the invention according to Examples 8 and 9.

As is depicted in FIG. 3, a starter culture (1) for the fermentation stage of the process is prepared by taking a small scale starter culture from a growing shake flask culture (Example 6) and inoculating therewith 9 L of growth medium, in a 14 L "Magnaferm" type fermentor (Example 7). The growth medium is the sea water-based medium supplemented with $KH_2PO_4$, $(NH_4)_2SO_4$, elemental sulfur and Tween-80 TM (Example 1), or alternatively, as noted in Example 1, it can be the sea water-based medium supplemented only with ammonium nitrate as nitrogen source for the bacteria.

The amount of innoculum taken from the growing shake flask culture to prepare the starter culture for fermentation is an amount sufficient to provide an initial cell count of about $2 \times 10^8$ cells/ml (or a total of about $18 \times 10^{11}$ cells in 9 L growth medium). The above inoculated medium is then stirred at 400-600 r.p.m and air is sparged from the bottom of the fermentor at a rate of 1-2 L/min in order to maintain a dissolved oxygen (DO) level of about 6 ppm. The pH of the culture is maintained at pH 3.0 by means of an automatic titrator (2) capable of introducing 5.0M KOH or 15% $NH_4OH$ into the culture. The culture is incubated for about 5 days or until the bacterial count reaches about $2 \times 10^9$ cells/ml of the culture. At the end of this growth cycle, the pH adjustment is disconnected and the pH is allowed to drop, due to sulfuric acid production by the bacteria, to between pH 1.2-1.5 during 3-5 additional days, the culture at this stage representing the starter culture (1).

The fermentation stage of the bioleaching process is then initiated by taking 5 L of the above starter culture (1) and concentrating the bacterial cells therein by microfiltration through a 0.45 μm microfiltration membrane cartridge (3) (0.45 μm cartridge of membrane area of 15 ft² housed in a Pelicon TM system, Millipore Corp., Ill., U.S.A.) and transferring the concentrated cell suspension into 35 L of fresh sea water medium (as above) in a 50 L plastic container equipped with a circulation device such as standard device employing a magnetically driven polypropylene head, and an air inlet (4). The initial titer of the bacteria in this fermentation culture medium is between $1-2 \times 10^8$ cells/ml. The initial pH of the fermentation culture medium is controlled by titration to be to pH 3.5 by the addition (5) of base such as 15% $NH_4OH$ as noted above. The fermentation culture is then grown until the pH of the culture drops to about pH 2.5, after about 1-2 days. At this stage the bioleaching step of the process is initiated by gradually adding 10 kg of washed CFA (6) to the above fermentation culture. The washed CFA (6) is prepared by taking the acidic supernatant (7) (about 5 L) of the above microfiltration stage, diluting it with sea water (8) (1:5 dilution) to obtain about 25 L of diluted supernatant in a suitable 40-50 L container equipped with a circulation device (9). 10 kg of CFA (10) (Example 3) is suspended in the diluted supernatant solution (9) and is washed by circulation of the suspension for about 1 hr. The circulation is stopped, the washed CFA (6) is allowed to settle and the supernatant of the wash solution (or neutralized solution) (11), now neutralised by the release of, for example, hydroxide ions during the washing of the CFA, is flushed out and discarded.

After addition of the washed CFA (6) to the fermentation culture (12) the pH of this culture is allowed to increase up to pH 4.0. If the pH increases to a higher value, due to release of, for example large amounts of hydroxide ions still present in the washed CFA, then the pH is adjusted to pH 4 by addition of sulfuric acid (13) or, if the pH is much less than 4.0 after addition of the washed CFA, then the aforesaid pH adjustment may be by adding base, e.g. $NH_4OH$, as indicated above, to reach a pH of about 4.0. The bioleaching fermentation (14) is then carried out by incubating the above culture under conditions of continual mixing and air supply (magnetically driven circulation and bottom air sparging) and with a culture temperature in the range of 25° C.-40° C. The incubation is continued until the pH of the culture reaches pH 0.5, this occurring usually within 2-3 weeks of fermentation. At this stage the bioleaching step is terminated by stopping the circulation and the air supply. The bioleached CFA then settles to the bottom of the container and the remaining turbid supernatant is pumped out of the container via a clarifier (15) such as, for example, a cyclon separator; and a microfiltration unit (16) being, for example, the above-noted 0.45 μm Pelicon ™ system, (Millipore Corp., Ill., U.S.A.) to provide a clear metal-bearing filtrate (17) (about 35 L) and a concentrated bacterial suspension (18). The settled bioleached CFA (19) is washed twice (20) with 30 L of fresh sea water. The first wash supernatant (21) is combined with the clear metal-bearing filtrate (17) and the second wash CFA suspension (or stabilized CFA) (22) is dumped or treated further. The above combined metal-bearing filtrate and first bioleached CFA wash (23) (total volume about 65 L) is then processed to obtain the various metals included therein as set forth in the following examples.

The above concentrated bacterial suspension (18) can be recycled to initiate another round of the bioleaching fermentation step, by way of adding this bacterial suspension to the microfiltered innoculum from the starter culture to provide an enhanced, i.e. rapid, initial fermentation growth phase (4) prior to the addition of another 10 kg batch of washed CFA (6). In this respect it should also be noted that the initial 9 L starter culture, from which 5 L were taken to carry out the above bioleaching process, can also be replenished for subsequent rounds of this process. In this case 5 L of fresh sea water medium is added to the remaining 4 L of starter culture (1) which is regrown to reach the aforesaid desired culture pH and cell number. This second round starter culture and subsequent ones reach the desired culture cell number and culture pH in much less time than the original one as the initial cell number is much higher, i.e. greater than $1 \times 10^9$ cells/mL.

EXAMPLE 9

Metal Recovery

As is also depicted in FIG. 3, the starting solution which is a combined metal-bearing filtrate and first wash supernatant (23) from the bioleached and washed CFA (Example 8) is processed to recover the various metals, e.g. Al, Ti, Fe and Co. This metal recovery process depicted in FIG. 3 for Titanium and Aluminium enrichments and subsequent purifications, is carried out by a series of metal precipitations (24)-(27) from the above starting solution (23). Each precipitation step is induced by the addition of 10N NaOH to the starting solution to cause an elevation of the pH of the solution resulting in metal precipitation from the solution. pH elevation is carried out in a stepwise manner to reach a desired pH at each step, and at each step the precipitated metal is collected. The final supernatant (28) from these precipitations is thus a neutralized solution which can be safely discarded together with the neutralized solution (11) from the CFA wash (6).

A summary of a typical metal precipitation profile obtained by this recovery process is presented in Table 4, from which it is apparent, for example, that most of the aluminium is precipitated from the solution at pH 3.1-4.7 and most of the titanium precipitated from the solution at pH 1.5-3.1.

The above precipitated metals, as is apparent from Table 4, however, represent enriched mixtures of the various metals and not the purified forms thereof. Further, Table 4 only provides selected examples of various metals precipitated in this way and does not give the full metal content of each precipitated fraction. To this end further tests were carried out to analyse the precipitated metal mixtures collected after a series of bioleaching runs and subsequent precipitations. the results of these tests are presented in Tables 5, 6 and 7, which relate to aluminium enriched powder, titanium enriched powder and cobalt enriched powder, respectively.

The aluminium enriched powder (Table 5) was analysed by taking 1.0 g of the above-described leachate precipitated at pH 3.1-4.7 and then dried, and dissolving it in 0.1N HCl followed by standard ICP analysis.

The titanium enriched powder (Table 6) was analysed by taking 1 g of two different samples, M1 and M2, each being dried leachates precipitated, as noted above, at pH 1.5, and then dissolving these in 0.1N HCl followed by standard ICP analysis.

Similarly, the cobalt enriched powder (Table 7) was analysed by taking a 1 g sample of a dried leachate precipitated at pH 9.0, dissolving it in 0.1N HCl and then analysing it by standard ICP analysis.

To obtain the desired metals in pure form from each of the above enriched powders, standard methods as known per se such as smeltering, etc. may be carried out.

TABLE 4

| Fraction No. | pH | Weight gr | Na | Ca | Al | Fe | Ti | SO4 | PO4 | weight of fraction | % from original weight |
|---|---|---|---|---|---|---|---|---|---|---|---|
| 1 | 1.5 | 0.24 | 0.04 | 0.004 | 0.002 | 0.001 | 0.0003 | 0.1 | 0.08 | 0.234 | 97.4 |
| 2 | 3.1 | 2.1 | 0.26 | 0.02 | 0.05 | 0.10 | 0.002 | 0.7 | 0.3 | 1.44 | 68.4 |
| 3 | 4.7 | 17 | 1.65 | 0.22 | 1.19 | 0.20 | 0.0 | 5.1 | 1.43 | 9.8 | 57.6 |
| 4 | 7.0 | 2 | 0.31 | 0.03 | 0.066 | 0.019 | 0.0 | 0.92 | 0.036 | 1.39 | 69.4 |

TABLE 5

Analysis of aluminium enriched powder

| Element | %/Weight |
|---|---|
| Na | 10.00 |
| Ni | <0.10 |
| Ca | 0.20 |
| Al | 7.92 |
| Mg | 0.50 |
| Fe | 1.30 |
| K | 0.40 |
| Ti | 0.062 |
| Mn | 2.10 |
| Co | <0.005 |
| S | 10.5 |
| Si | 1.9 |
| P | 2.7 |

TABLE 6

Analysis of titanium enriched powders

| Element | %/Weight M1 | %/Weight M2 |
|---|---|---|
| Na | 1.00 | 0.10 |
| Ni | <0.10 | <0.10 |
| Ca | 0.30 | 0.30 |
| Al | 6.58 | 6.05 |
| Mg | 0.80 | 0.80 |
| Fe | 8.60 | 10.00 |
| K | 0.20 | 2.40 |
| Ti | 0.218 | 0.253 |
| Mn | <0.10 | <0.10 |
| Co | 0.054 | 0.050 |
| S | 8.60 | 8.70 |
| Si | 2.70 | 2.70 |
| P | 4.90 | 5.70 |

TABLE 7

Analysis of cobalt enriched powder

| Element | %/Weight |
|---|---|
| Na | 12.40 |
| Ni | 0.60 |
| Ca | 0.50 |
| Al | 0.19 |
| Mg | 11.70 |
| Fe | <0.10 |
| K | 0.20 |
| Ti | <0.005 |
| Mn | 2.10 |
| Co | 0.816 |
| S | 11.9 |
| Si | 0.3 |
| P | <0.1 |

The bioleaching and metal recovery process set forth in Examples 8 and 9 above, was repeated a number of times and compared also to the leaching of CFA by using only mineral acid (1.0M $H_2SO_4$), and the following conclusions and additional observations were made:

(a) The Thiobacilli interact with CFA particles via the sulfuric acid they produced in culture. The titanium is leached mainly where pH 1.0, usually within several days after maximal culture growth was obtained. Toxic elements such as molybdenum, selenium and boron leached out when the pH of the cultures dropped to about pH 1.4, rendering the treated CFA non-toxic at this stage.

(b) When mineral acid is applied the aluminum is leached out in two stages:
(i) a rapid stage which lasts 24 hrs; and
(ii) a slow stage of constant rate for about 35 days.

(c) The leaching yields of aluminium and titanium were influenced mainly by temperature when mineral acid was used as leaching agent. With 1% CFA the yield was doubled when temperature was increased from 30° to 60° C., i.e. yield increased from 10% to 20%. Also, the duration of incubation at desired pH influenced the yield: the longer the incubation the higher the yield. The increase in yield due to prolonged incubation becomes insignificant after 24 hrs when mineral acid is applied. However, when *Thiobacillus thiooxidans* cultures are applied it is important to keep the acid acting for longer durations since the acid concentration is lower, and since acid is produced throughout the incubation, the leaching yield of the above metals is thus influenced by duration of culture at desired pH for leaching of these metals as noted above. Leaching yields of the metals by the bioacid, i.e. produced by the Thiobacilli (about 0.2M $H_2SO_4$ in fermentation cultures) matched those obtained with mineral acid (1.0M $H_2SO_4$), although the process lasted somewhat longer, this being negated by the fact that leaching with mineral acid is far more expensive requiring large amounts of acid, machinery that is acid resistant, and large amounts of base to neutralize the acidic by-products before disposal thereof.

(d) Optimized growth of Thiobacilli was achieved in the sea water-based medium, supplemented with 1% elementary sulfur, ammonium nitrate and up to 50% CFA, at pH values of about pH 3.0. The best leaching rates of aluminium, up to about 14%, and titanium, up to about 20% of the amount originally present in the CFA, were obtained in the above cultures supplemented, however, with only 10-20% CFA. For best results the cultures have to be well aerated and agitated, to support growth of over $1 \times 10^9$ cells/ml that lead to a pH lowering to pH 0.8–0.6 thereafter.

With respect to the bioleaching process and subsequent metal recovery as set forth above (Examples 8 and 9) it is apparent that this is an environmentally friendly procedure on the one hand, and economically viable on the other in view of the amounts of aluminium, titanium and cobalt in the enriched powders. When considering that many millions of tons of CFA are produced annually world-wide, the above procedure can be applied on a large scale to obtain many tons of these valuable metals. The process itself is inexpensive utilizing recyclable sulfuric acid producing bacteria in relatively cheap fermentation machinery and culture media (sea water being abundant and free). The by-products of the process are non-toxic and can be safely dumped, the bio-extracted CFA may even be used as, for example, landfill material or soil fertilizer. Although only a fraction of the metals originally present in the CFA are extracted (as apparent from Tables 4-7), the metals remaining in the bio-extracted CFA represent, however, those which are extremely difficult to dissolve, i.e. they will not leach out when this treated CFA is subjected to normal environmental conditions including exposure to so-called "acid rain". Further, the metal recovery process involves precipitation of metals, using a base, from acidic metal-bearing solutions, with the result that the supernatants to be discarded have essentially neutral pH and as such are environmentally acceptable.

We claim:

1. A bioleaching process for the extraction of metals from coal fly ash (CFA) comprising the steps:
   (a) producing an acidic culture medium by incorporating in a sea water solution a nutrient supplement including at least a nitrogen source, suspending therein CFA in the amount of 10-50% w/v and adding sulfuric acid until an initial pH within the range of about 2.5 to about 4.0 is attained;
   (b) innoculating into said culture medium a microorganism culture which comprises at least one strain of Thiobacillus thiooxidans capable of growing and producing sulfuric acid in said acidic culture medium;
   (c) establishing aerobic conditions in the innoculated culture medium by aeration and agitation and maintaining aerobic conditions to induce fermentation until the pH of the fermentation culture decreases to a level at which leachable metals are leached from said CFA;
   (d) interrupting the aeration and agitation to enable separation of said fermentation culture into a CFA raffinate sediment and a supernatant comprising a suspension of the Thiobacillus thiooxidans cells and the extracted metals, and separating the supernatant from the sediment;
   (e) subjecting said supernatant to microfiltration to separate the Thiobacillus thiooxidans cells whereby a metal-bearing filtrate and a concentrated suspension of the Thiobacillus thiooxidans cells are separately obtained;
   (f) fractionating the metal-bearing filtrate by stepwise raising the pH thereof by the addition of a desired amount of a suitable base to precipitate a metal containing fraction, and collecting a metal containing fraction after each precipitation.

2. A process according to claim 1, wherein the culture medium contains 10-20% w/v CFA.

3. A process according to claim 1, wherein said at least one Thiobacillus thiooxidans strain is derived from a natural environment and the culture medium is supplemented with sources of phosphorus, nitrogen and sulfur.

4. A process according to claim 3, wherein the culture medium is supplemented with potassium phosphate, ammonium sulfate, elemental sulfur and a surfactant.

5. A process according to claim 1, wherein said microorganism culture is a selected, acclimatized, Thiobacillus thiooxidans culture previously grown for an extended period in the presence of CFA, and the culture medium is supplemented with a nitrogen source only.

6. A process according to claim 5, wherein said nitrogen source is ammonium nitrate.

7. A process according to claim 1, wherein the Thiobacillus thiooxidans culture used for innoculation is prepared by culturing Thiobacillus thiooxidans in an acidic, supplemented sea water solution having an initial pH of about 2.5-4.0, in the absence of CFA, until the cell count reaches about $2 \times 10^9$ cells/ml and the pH of the culture medium drops to about 1.2-1.5, and micro-filtering the resulting culture whereby a concentrated cell suspension and an acidic filtrate are separately obtained.

8. A process according to claim 1, wherein Thiobacillus thiooxidans ZYR 1, NCIMB 40453, is used.

9. A process according to claim 1, wherein the CFA introduced into said culture medium is first washed with an acidic solution to remove hydroxide ions from the CFA.

10. A process according to claim 9, wherein the washing is performed with a sea water solution containing the acidic filtrate obtained in accordance with claim 7.

11. A process according to claim 1, wherein the fermentation is terminated when the pH of the fermentation culture in step (c) has reached a value below 2.0.

12. A process according to claim 11, wherein the fermentation is terminated when the pH of the fermentation culture has reached a value of about 1.5 or less.

13. A process according to claim 12, wherein the fermentation is terminated when the pH of the fermentation culture has reached a value of between 0.4 and 1.0.

14. A process according to claim 13, wherein the fermentation is terminated when the pH of the fermentation culture has reached a value of between 0.6-0.8.

15. A process according to claim 1, wherein said CFA raffinate obtained in step (d) is collected and washed with fresh sea water to remove extracted metal entrapped in the raffinate sediment.

16. A process according to claim 15, wherein the sea water from a first wash of said CFA raffinate is recycled and combined with the filtrate obtained in step (e) in claim 1 for metal extraction.

* * * * *